United States Patent [19]
Barreras et al.

[11] Patent Number: 5,318,596
[45] Date of Patent: Jun. 7, 1994

[54] ACTIVITY SENSING PACEMAKER

[75] Inventors: Francisco J. Barreras, Miami; Oscar Jimenez, Coral Gables, both of Fla.

[73] Assignee: Exonic Corporation, Miami, Fla.

[21] Appl. No.: 791,423

[22] Filed: Nov. 13, 1991

[51] Int. Cl.⁵ ............................................. A61N 1/365
[52] U.S. Cl. ........................................ 607/19; 128/782
[58] Field of Search ................ 128/419 PG, 782, 670, 128/419 P, 774, 739, 740; 607/19, 18, 17

[56] References Cited

U.S. PATENT DOCUMENTS

| | | | |
|---|---|---|---|
| 4,140,132 | 2/1979 | Dahl | 128/419 PG |
| 4,771,780 | 9/1988 | Sholder | 128/782 |
| 4,846,195 | 7/1989 | Alt | 128/782 |
| 4,860,751 | 8/1989 | Callaghan | 128/419 PG |
| 4,869,251 | 9/1989 | Lekholm et al. | 128/419 PG |
| 4,896,068 | 1/1990 | Nilsson | 128/419 PG |
| 4,945,909 | 8/1990 | Fearnot et al. | 128/419 PG |
| 5,040,533 | 8/1991 | Fearnot et al. | 128/419 PG |
| 5,040,535 | 8/1991 | Mann et al. | 128/419 PG |
| 5,233,984 | 8/1993 | Thompson | 607/19 |

Primary Examiner—William E. Kamm
Assistant Examiner—Kennedy J. Schaetzle
Attorney, Agent, or Firm—Thomas R. Vigil

[57] ABSTRACT

The activity sensing pacemaker comprises: a heart pulse sensing device for sensing heart pulses; pulse generating circuitry for generating pacing pulses; activity sensing structure and circuitry for sensing activity/movement of a patient wearing the pacemaker in one or more of three directions/dimensions, x, y, z, and for causing the pulse generating circuitry to generate pacing pulses at a rate/frequency related to the movements sensed; and, control circuitry coupled to the heart pulse sensing device, to the pulse generating circuitry and to the activity sensing structure and circuitry for controlling the pulse generating circuitry in response to the heart pulses sensed or in response to the patient movements sensed, the activity sensing structure and circuitry causing generation of control pulses related to the movements of the patient and the control circuitry including frequency sensing circuitry for sensing the frequency of the control pulses generated and for controlling the rate/frequency of the pacing pulses generated by the pulse generating circuitry relative to the frequency of the control pulses generated by the movements of the patient in one or more directions/dimensions, x, y, z, independent of the duration or amplitude of the control pulses.

30 Claims, 4 Drawing Sheets

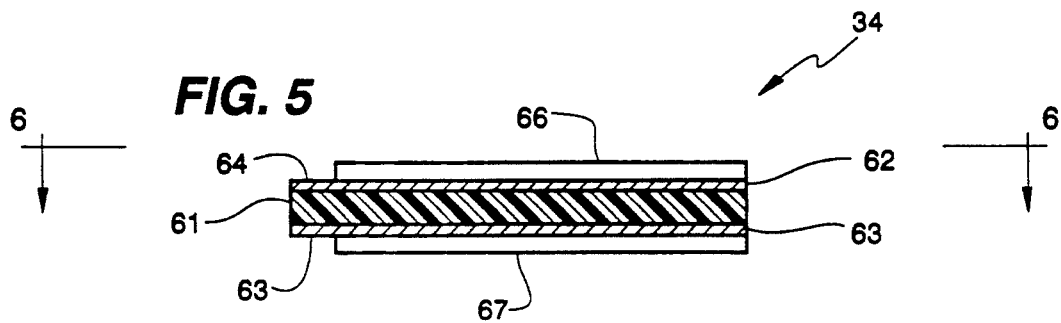
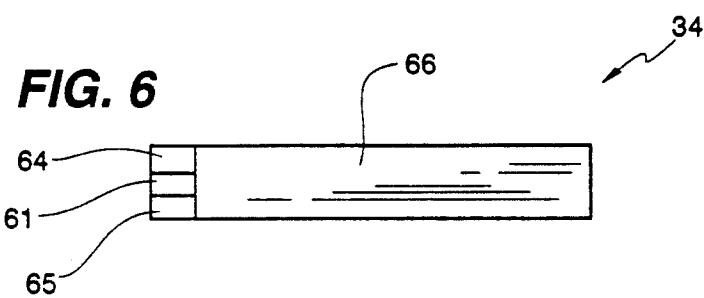
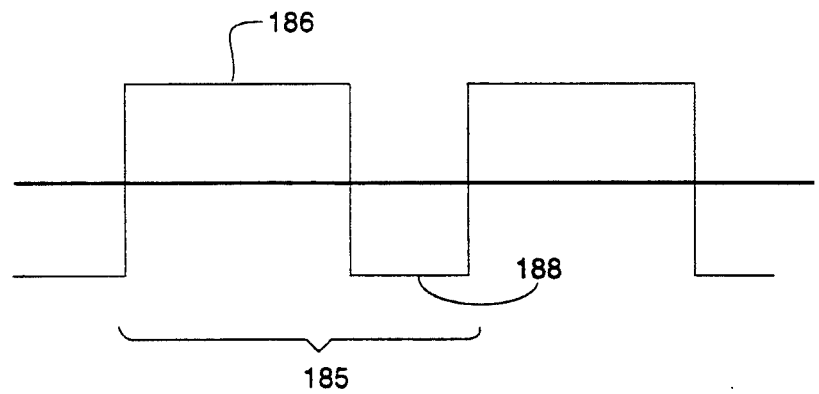

ACTIVITY SENSING PACEMAKER

BACKGROUND OF THE INVENTION

1. Field of the Invention.

The present invention relates to an activity sensing pacemaker which senses activity or motion along several different axes, such as the X axis, the Y axis and the Z axis, utilizing an array of motion sensors or accelerometers and to pulse generating circuitry for controlling the output of heart stimulus pulses relative to the level of activity sensed.

2. Description of the related art including information disclosed under 37 CFR §§ 1.97-1.99.

Heretofore, various activity sensing pacemakers have been proposed. Examples of these previously proposed activity sensing pacemakers are disclosed in the following U.S. patents:

| U.S. Pat. No. | Patentee |
| --- | --- |
| 4,140,132 | Dahl |
| 4,428,378 | Anderson et al. |
| 4,771,780 | Sholder |
| 4,846,195 | Alt |
| 4,860,751 | Callaghan |
| 4,869,251 | Lekholm et al. |
| 4,896,068 | Nilsson |
| 4,913,145 | Stotts |
| 4,940,052 | Mann et al. |
| 4,940,053 | Mann et al. |
| 5,010,893 | Sholder |

The Dahl U.S. Pat. No. 4,140,132 discloses a variable rate timer for a cardiac pacemaker including a piezoelectric element, a rectifier for rectifying the signals generated by the piezoelectric element and a capacitor network which receives the rectified pulses from the rectifier and stores those pulses therein. The stored pulses are supplied to the gate of a field effect transistor where a level or charge of voltage stored controls the current to the transistor which is used to control the pacing or timing rate of the pacemaker.

The activity sensing pacemaker of the present invention differs from the Dahl patent by sensing activity or motion along several different axes, preferably three axes, and does not rectify voltage generated by a piezoelectric element and does not have a voltage circuit including a constant timing resistor or a timing capacitor.

The Anderson U.S. Pat. No. 4,428,378 teaches a motion sensor that supplies signals to a level detector and band pass amplifier so that pulses above a certain level and within a certain frequency band only, are integrated to provide a control signal for controlling pacing.

The Sholder U.S. Pat. No. 4,771,780 teaches an activity sensor comprising a moving conducting element within a housing, as does the Lekholm et al. U.S. Pat. No. 4,869,251. In Lekholm et al. there is provided a hollow member with a freely movable member therein, the freely movable member generating a mechanical vibration upon movement by a patient. A transducer senses the vibration and generates an electrical signal corresponding to the mechanical vibrations. The electrical signal is proportionate to the movement and is used to vary the stimulation rate. In Sholder the moving conducting element within the cylindrical housing makes and breaks electrical contacts between at least two of a plurality of electrodes in the housing, the making and breaking of contacts being indicative of motion or activity of the patient.

The Alt U.S. Pat. No. 4,846,195 discloses an implantable position and motion sensor which includes a housing having a circular disc-like wall of electrically insulative material with conductive pins extending therethrough, a lid portion over the circular disc-like wall and a mercury ball within the housing and movable between the pins for effecting conduction between the pins. Movement of the mercury ball between the pins and the lid portion will generate signals indicating activity or movement of the patient and the position of the mercury ball indicates whether the patient is standing or lying down.

The Callaghan U.S. Pat. No. 4,860,751 teaches a passive activity sensor for a pacemaker requiring no power for sensing physical activity and a physical activity threshold detector.

The Nilsson U.S. Pat. No. 4,896,068 teaches the construction of an activity sensor having two individual or inter-related piezoceramic parts arranged side by side which are oppositely polarized and which are secured to a flat wall of a pacemaker housing.

The Stotts U.S. Pat. No. 4,913,145 discloses a cardiac pacemaker which has a sense amplifier for passing signal components lying in a selectively variable pass band.

The Alt U.S. Pat. No. 4,926,863 teaches the use of an accelerometer in a rate responsive cardiac pacemaker for sensing body movement and then selects only a portion of the electrical signal generated by the accelerometer at a frequency rate below 4 Hz to discriminate against signal components arising from other than physical exercise of the patient.

The Mann et al. U.S. Pat. No. 4,940,052 discloses a processor in a pacemaker which converts a raw signal generated by an activity sensor (a piezoelectric sensor) to a sensor-indicator rate signal in accordance with a selectable transfer relationship which defines the sensor-indicator rate signals as a function of a set of discrete sensor level index signals. The selected sensor level index signals is related to the energy content of the raw signal. Then, the selective sensor level index signal is used to control the pacing rate from a pulse generator.

The Mann et al. U.S. Pat. No. 4,940,053 discloses a rate responsive pacemaker having a piezoelectric sensor and a raw signal energy converter which amplifies the raw signal, rectifies the raw signal and then integrates the area of the raw signal in one embodiment of the energy converter.

In another embodiment of the energy converter, the durations of each rectified pulse of the raw signals are counted, individual duration counts are summed over a period of time (integrated) and the sum is utilized as an indication of the energy content of the raw signal. The level of the energy content is used to control the pacing rate of a pacemaker.

The Sholder U.S. Pat. No. 5,010,893 discloses a motion sensor mounted in a pacemaker. The motion sensor includes an enclosed housing having a movable conductive element therein that partially fills the space in the housing and is free to flow or otherwise move around the inside of the housing in response to external forces. As the conductive element moves within the enclosed housing, it makes electrical contact with at least two of three electrodes that are selectively spaced around the periphery of the housing in a manner similar to the movement of a contact in the earlier Sholder patent and the mercury ball in the earlier Alt patent.

SUMMARY OF THE INVENTION

According to the present invention, there is provided an activity sensing pacemaker comprising: a heart pulse sensing device for sensing heart pulses; pulse generating circuitry for generating pacing pulses; activity sensing structure and circuitry for sensing body movements of a patient wearing the pacemaker relative to the chest of the patient in specific ones of three dimensions or directions extending along an x axis, a y axis, or a z axis, and independent of the force of gravity, the activity sensing structure and circuitry including first structure for sensing activity along a first one of the three axes and second structure for sensing activity along a second one of the three axes; and, control circuitry coupled to the heart pulse sensing device, to the pulse generating circuitry and to the activity sensing structure and circuitry for controlling the pacing frequency of the pacing pulses generated by the pulse generating circuitry either in response to the intrinsic heart rhythm of the patient sensed by the heart pulse sensing device or in response to the direction and frequency of the patient's body motions sensed by the activity sensing structure and circuitry in or along at least two of said three axes, x, y, or z, relative to the patient's chest.

The control circuitry controls a pulse generator relative to the frequency of pulse signals from the activity sensing devices and circuitry independent of the amplitude or duration of the pulse signals.

The control circuitry includes programming in a program memory and a multivibrator (a) for enabling the multivibrator to pass only signals received relative to the activity/movement along one, two and/or three of the axes along which activity/movement is sensed and/or (b) for requiring that there be signals on all three axes in order for there to be output pulses at the output of the monostable multivibrator.

Also according to the present invention there is provided an activity sensing pacemaker comprising: a heart pulse sensing device for sensing heart pulses; pulse generating circuitry for generating pacing pulses; activity sensing structure and circuitry for sensing activity/movement of a patient wearing the pacemaker in one or more of three directions/dimensions, x, y, z, and for causing the pulse generating circuitry to generate pacing pulses at a rate/frequency related to the movements sensed; and, control circuitry coupled to the heart pulse sensing device, to the pulse generating circuitry and to the activity sensing structure and circuitry for controlling the pulse generating circuitry in response to the heart pulses sensed or in response to the patient movements sensed, the activity sensing structure and circuitry causing generation of control pulses related to the movements of the patient and the control circuitry including frequency sensing circuitry for sensing the frequency of the control pulses generated and for controlling the rate/frequency of the pacing pulses generated by the pulse generating circuitry relative to the frequency of the control pulses generated by the movements of the patient in one or more directions/dimensions, x, y, z, independent of the duration or amplitude of the control pulses.

BRIEF DESCRIPTION OF THE DRAWINGS

FIG. 5 is a longitudinal sectional view of a piezoelectric film which can be used as part of one of the piezoelectric sensors shown in FIG.'S. 2 or 4.

FIG. 6 is a top plan view of the piezoelectric film shown in FIG. 5.

FIG. 9 is a graph of a cycle of the output signal from a bistable oscillator in the circuitry shown in FIG. 7.

BRIEF DESCRIPTION OF THE PREFERRED EMBODIMENT(S)

Figure 1:
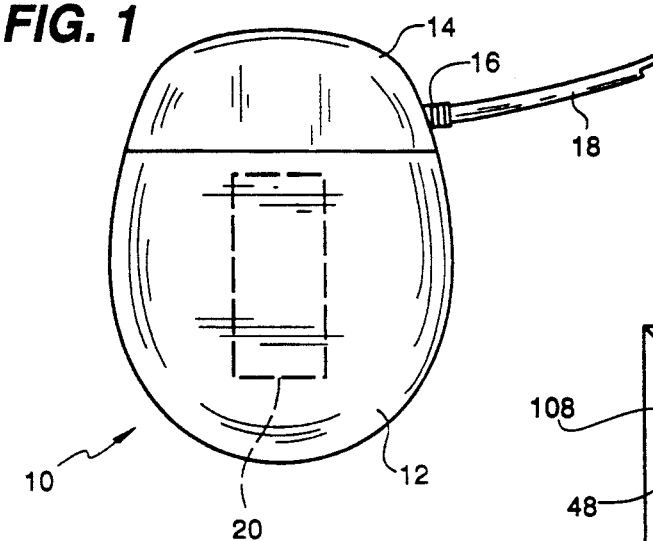
FIG. 1 is a side elevational view of a pacemaker having mounted therein applicant's activity sensor.

Referring now to the drawings in greater detail, there is illustrated in FIG. 1 a cardiac pacemaker 10 comprising a lower case or can 12, and an upper top or neck 14 which receives the proximal end portion 16 of a pacing lead 18.

Shown in dotted lines within the case 12 is an activity sensor 20 constructed according to the teachings of the present invention.

Figure 2:
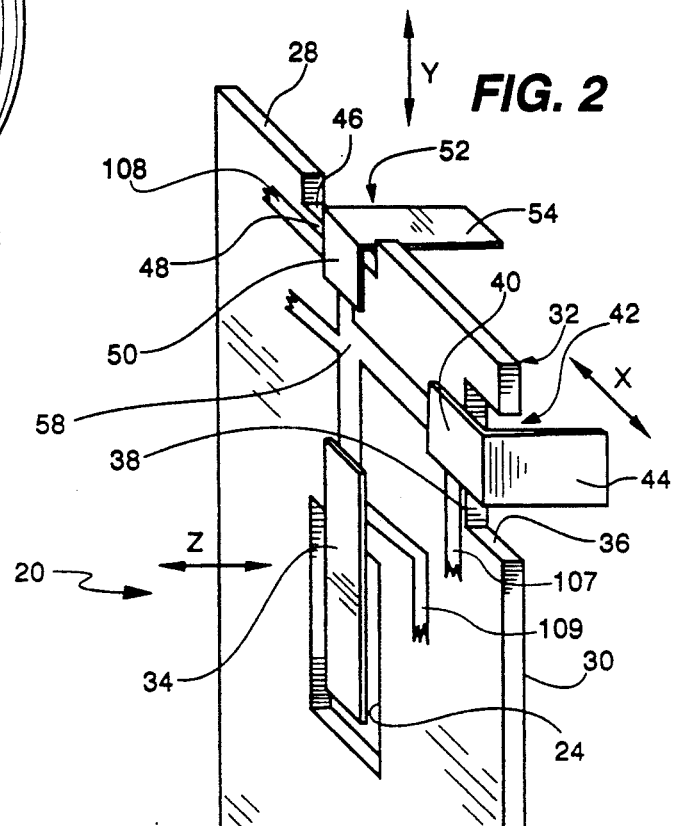
FIG. 2 is a perspective view of one embodiment of the activity sensor constructed according to the teachings of the present invention and shows a plate with three piezoelectric sensors for sensing activity along three different axis, the X axis, the Y axis and the Z axis.

In FIG. 2, there is shown one embodiment of the activity sensor 20 of the present invention. Here it will be seen that the activity sensor 20 comprises a plate 22 having a hole 24 therein. The plate is non-metallic, typically a printed circuit board, and has a top edge 28 and a right side edge 30 joining at an upper right hand corner 32 of the plate 22. A cantilevered piezoelectric sensor 34 is mounted on the plate adjacent the hole 24. This piezoelectric sensor 34 is cantilevered over the first hole 24 and will vibrate when the plate 22 is moved along the Z axis of the plate 22.

The plate 22 has along the right side edge 30 thereof a notch 36 near the upper right hand corner 32 and a portion 38 of the plate 22 adjacent the notch 36 supports a base leg 40 of a piezoelectric sensor 42 which has a bent outer leg 44 which extends outwardly from the plate 22 and is positioned to be moved or vibrated when there is movement along the X axis of the plate 22, as shown in FIG. 2.

Then, on the top edge 28 of the plate 22 there is provided another notch 46 and a portion 48 of the plate 22 adjacent that notch 46 supports a base leg 50 of another piezoelectric sensor 52 which has an outer leg 54 which extends outwardly from the plate 22 and at a right angle to the piezoelectric sensor 34 and from the outwardly extending leg 44 of the piezoelectric sensor 42, and is positioned to vibrate when there is movement along the Y axis of the plate 22, as shown in FIG. 2.

One terminal or tab of each piezoelectric sensor is connected to a ground or common 58 for a pacemaker system, such ground being a conductive strip 58 on a printed circuit on the plate 22. The signals produced from each of the piezoelectric sensors 42, 52 and 34 are referred to as signals generated either along the X axis, the Y axis or the Z axis and are supplied to rate control circuitry 60 which will be described in greater detail in connection with the description of FIG. 7.

Figure 3:
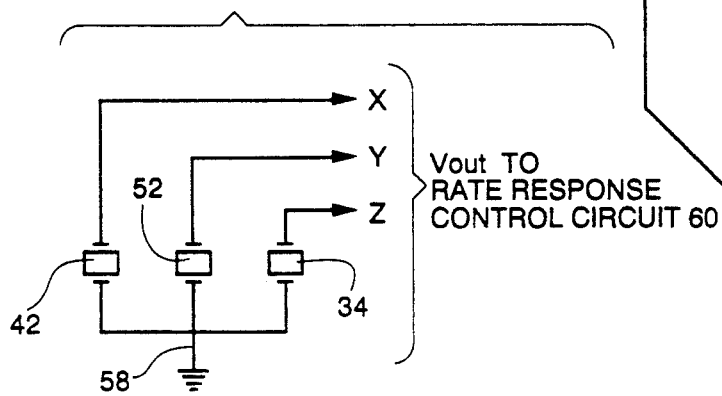
FIG. 3 is a simplified schematic circuit diagram of the output from the piezoelectric sensors of the activity sensor shown in FIG. 2.
Figure 7:
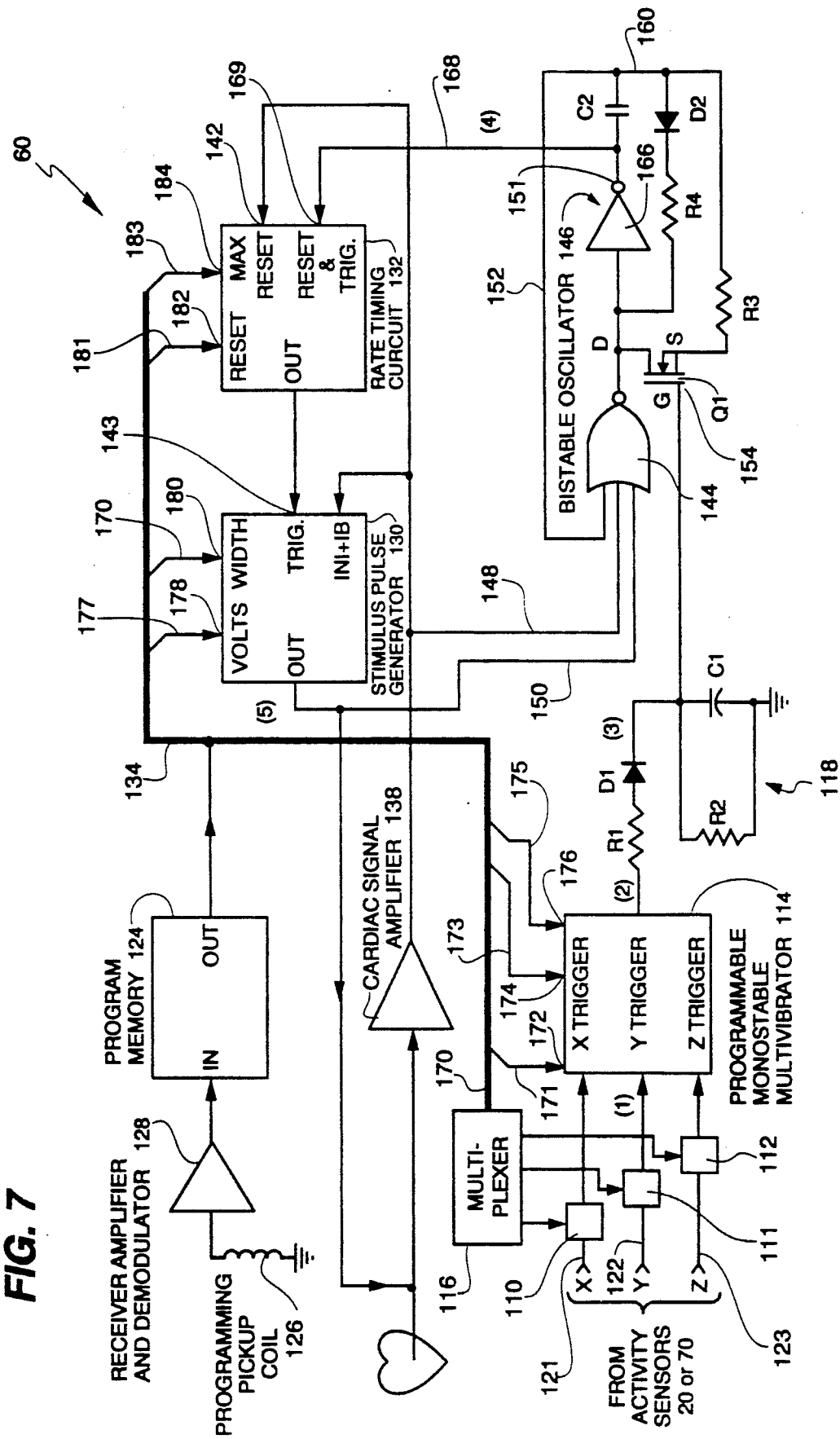
FIG. 7 is a schematic circuit diagram of the activity sensor processing and pulse generating circuitry which processes and utilizes the signals from the piezoelectric sensors for controlling the generation of pacing pulses.

FIG. 3 shows the connection of each of the piezoelectric sensors 42, 52 and 34 to ground or common 58 and shows the output signals identified as X, Y and Z which are supplied to the circuitry 60 shown in FIG. 7.

The activity sensor 20 shown in FIG. 3 can be referred to as a tri-axial reed activity sensor comprising three sensors or reeds 42, 52 and 34 with a PVDF piezofilm bonded along its longitudinal plane and mechanically held at only one end to allow the other end to flex or vibrate freely. Such a reed sensor is shown in FIG'S. 5 and 6. The reeds 42, 52 and 34 can be made from many materials having memory, such as spring steel and some plastics. Each reed 42, 52 or 34 is oriented in a different axis in order to sense motion in the X, Y or Z axis as described above.

An example of the construction of one embodiment of the piezoelectric sensor 34 is shown in FIG'S. 5 and 6. Here it will be seen that a piezofilm 61 has metalized upper and lower conductive films 62 and 63 thereon terminating at one end in electrode tabs 64 and 65. The conductive films 62 and 63 each have an outer protective coating 66 or 67.

As the patient's physical activity develops motion in any one of the three axes or combination thereof, the reeds 42, 52 and 34 will flex, stretching the piezofilm which generates an electrical signal whose intensity corresponds to displacement acceleration forces induced by the patient. These electrical signals are processed and converted into a pacing rate by the circuitry 60 shown in FIG. 7.

Figure 4:
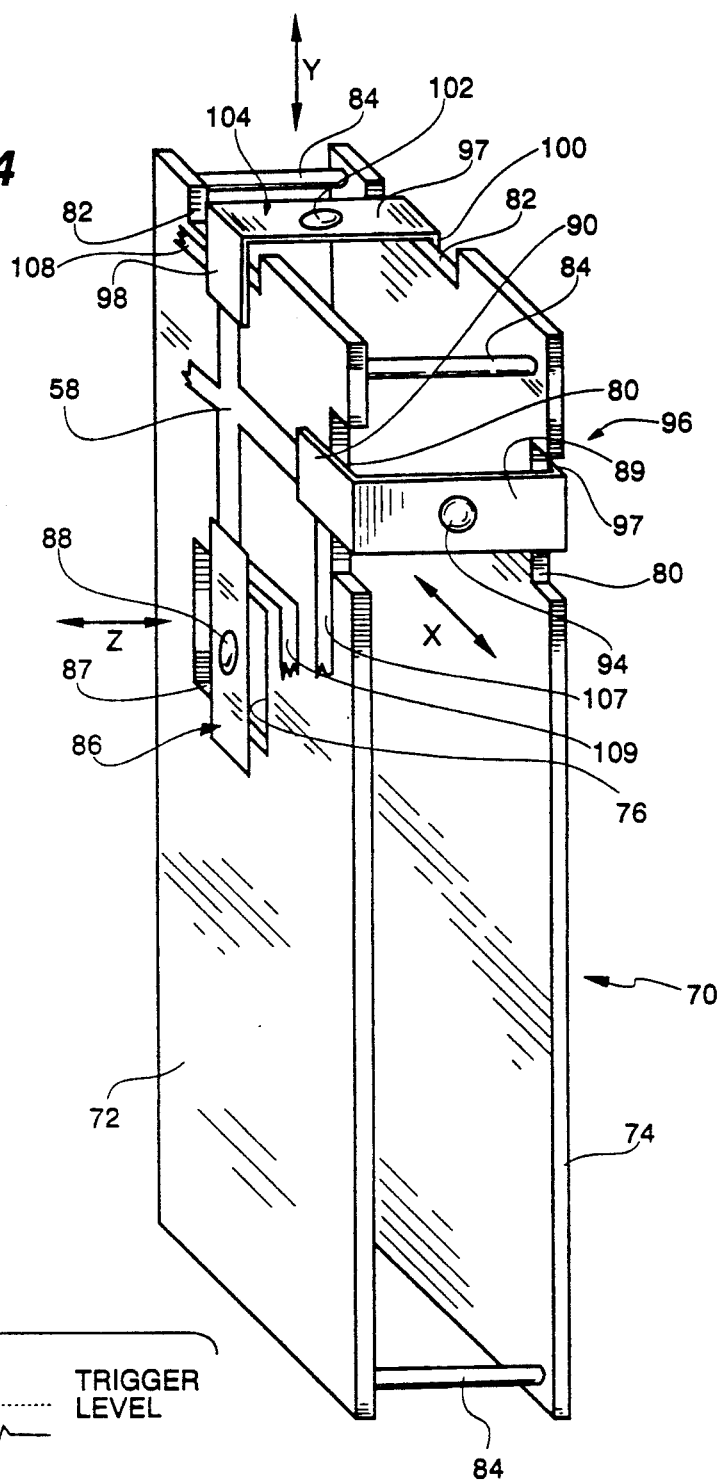
FIG. 4 is a perspective view of another embodiment of an activity sensor constructed according to the teachings of the present invention which comprises two parallel spaced plates with two piezoelectric sensors mounted between the plates for sensing activity along two different axes, e.g. the X axis and the Y axis and a piezoelectric sensor mounted along in the X-Y plane for sensing activity along the Z axis.

In FIG. 4 there is illustrated another embodiment of an activity sensor 70 constructed according to the teachings of the present invention. The activity sensor 70 comprises two spaced apart plates 72 and 74 with the upper plate 72 being substantially identical to the lower plate 74, each plate 72, 74 having a hole 76 and two notches 80 and 82. The plates 72, 74 are held in a spaced apart relationship by four corner pins 84. Extending across the hole 76 is a first piezoelectric sensor 86 which is made of a polyvinylidene film 87 having a weight 88 in the middle thereof, such as a ball bearing. This piezoelectric sensor 86 senses movement along the Z axis.

Then, a film 89 of piezoelectric polyvinylidene film supported between two base tabs 90 and 92 extending between the notches 80 and having a weight 94, such as a ball bearing, in the middle thereof defines a second piezoelectric sensor 96. This piezoelectric sensor 96 senses movement along the X axis.

Finally, another film 97 of piezoelectric polyvinylidene film positioned between two base tabs 98 and 100 and extending between the notches 82 and having a weight 102 in the middle thereof defines a third piezoelectric sensor 104.

The notches 80 and 82 allow the piezoelectric sensors 96 and 106 to be recessed within the rectangular edges of the plates 72 and 74.

Stated another way, FIG. 4 illustrates another tri-axial activity sensor 70 comprising three piezoelectric sensors 86, 96 and 104 defined by three strips 87, 89 and 97 of PVDF piezofilm, with a heavy object 88, 94 and 102, such as a ball bearing, bonded at the center, mechanically held at both ends in order to allow the center portion of the film 87, 89 and 97 to flex freely. Each piezofilm strip 87, 89, 97 is oriented in a different axis in order to sense motions in the Z, X and Y axes and has one electrode tab thereof connected to a system ground or common 58 and another electrode tab connected to an input line 107, 108 or 109 to the circuitry 60 shown in FIG. 7. As the patient's physical activity develops motion in any one of the three axes, or combination thereof, the piezofilm(s) 88, 94 and 102 will stretch generating electrical signals whose intensity corresponds to the displacement and acceleration forces induced by the patient. Again, these electrical signals are processed and converted into a pacing rate by the circuitry 60 shown in FIG. 7.

Polyvinylidene fluoride (PVDF) piezofilm is used as an example of a material having required piezoelectric properties for use in the activity sensors 20 and 70 of the present invention. However, the activity sensors 20 and 70 of the present invention are not to be limited to the use of PVDF piezofilm. Other piezoelements may be used including polymeric ferro-electric and bimorph type of sensors.

For illustration purposes, the activity sensors 20 and 70 shown in FIGS. 3 and 4 employ PVDF piezofilm. PVDF piezofilm should be considered as a dynamic material that develops an electrical charge proportional to changes in mechanical stress or strain. External forces applied to the film results in compressive or tensile strain and the film develops a proportionate open circuit voltage. Exposure to a reciprocating force results in a corresponding alternating electrical signal. The frequency response ranges widely—0.005 Hertz to gigaHertz. The piezoelectric properties of PVDF depend heavily on the degree and type of its crystalline structure. Three common crystalline phases for the material are designated: alpha, beta and gamma. To obtain significant piezoelectric activity, beta phase polymer must be "poled". Poling exposes the polymer to a high electric field at elevated temperatures.

Although the activity sensors 20 and 70 sense activity or motion in three different axes, e.g. the X axis, the Y axis and the Z axis, the activity sensor 20 or 70 can be constructed to sense activity or motion in different axes other than the three axes indicated.

Also, two or more piezoelectric sensors can be mounted on each axis along which motion is to be detected within the pacemaker housing and separate from the wall of the housing and in position to generate electrical signals when the pacemaker wearer engages in physical exercise, such as running or swimming.

Referring now to FIG. 7 voltage signals are then generated from the motion sensed in selected axes of the three axes. Each small voltage signal generated by one of the piezoelectric sensors 34, 42 and 52 or 86, 96 and 104 is supplied through a multiplex switch 110, 111 and 112 in each of the input lines 107, 108 or 109 to a programmable monostable multivibrator 114, as shown in FIG. 7.

Figure 8:
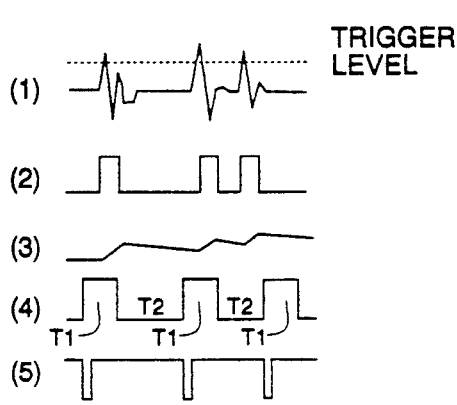
FIG. 8 is a timing diagram of the signals at five different points in the circuitry shown in FIG. 7.

The monostable multivibrator or one shot 114 converts the analog signals, graph (1) in FIG. 8, from each piezoelectric sensor 42, 52, 34 or 96, 104, 86 into a larger digital pulse. The number of larger digital pulses is representative or indicative of the frequency of the motion generated pulses and are independent of the amplitude or duration of the motion generated pulses. In this respect, the one shot 114 acts as an amplifier for generating an output pulse of constant width and amplitude, graph (2) in FIG. 8, each time a motion generating pulse is received depending upon the axis or axes selected by a multiplexer 116 controlling the switches 110-112. These pulses from the one shot or monostable multivibrator 114 are supplied through a resistor R1 and a diode D1 to a capacitor C1 which has a discharging resistor R2 connected thereacross. The resistor R1 and capacitor C1 form an integrating circuit 118.

Stated otherwise, the larger digital pulses from the one shot 114 charge the capacitor C1 to a DC level dependent upon the frequency of the pulses and their level, graph (3) in FIG. 8, independent of the amplitude or duration of the signals from the activity sensors 20 or 70. The capacitor C1 discharges through the high resistance resistor R2 such that the voltage level on the capacitor C1 represents the average activity level (number of pulses/unit of time) of the pacemaker wearer in the axial direction of the particular axis or axes along which activity is sensed.

Programmable selection of the axis or axes along which motion is to be sensed is provided by the multiplexer 116 which is connected to the multiplexer switches 110, 111 and 112 in input lines 107, 108 and 109 for the X, Y and Z axes. The multiplexer 116 is controlled by a software program in a program memory 124, and this program in the memory 124 can be adjusted by means of a program pickup coil 126 mounted inside the pacemaker case 12. Programming signals are picked up by the coil 126, amplified and demodulated by an amplifier/demodulator 128 and then supplied to the program memory 124. The program memory 124 then supplies suitable control signals to the multiplexer 116, to a stimulus pulse generator 130 and to a rate timing circuit 132 via a bus 134.

In this way, motion sensed along each single axis X, Y or Z can be non-invasively, enabled or disabled, by the pacemaker programmer thus allowing the physician to determine the motion axis or axes that will best sense activity for a particular type of exercise so that activity along that axis or axes can be used to adjust the pacing rate or escape interval of the pacemaker.

While three capacitors C1 could be utilized, one for each motion axis, the preferred embodiment uses the multiplexer 116 controlled by the program memory for transmitting each axis sensor raw signal to the corresponding trigger input, graph (1) of FIG. 8, of the one shot 114. Programmable selection of axes to be sensed is controlled by the multiplexer 116. Each multiplexer switch 110, 111 and 112 can be permanently disabled from memory in order to deactivate motion sensing in that particular axis. To activate motion detection in the given axis, that particular multiplexer switch 110-112 is simply allowed to multiplex.

Programmable selection of each independent trigger level to the one shot 114 is provided (one per axis) thus permitting independent sensitivity adjustment for each axis. This will allow the physician to better adapt the pacemaker 10 to the type of motion generated by the type of sport or activity typical for each patient.

Programmable modes of activity sensing through "OR" and "AND" modes is provided. In the "OR" mode, signals from one of the enabled axis or axes rising above the trigger level will cause adjustment in pacing rate. The "OR" mode may be used to cause an adjustment of the pacing rate when the patient engages in strenuous types of activities that generate small motions, such as weight lifting.

In the "AND" mode, all enabled axes must generate signals above the trigger level in order to cause an adjustment of the pacing rate. The "AND" mode may be used by the pacemaker 10 to ignore body motions in any single axis which typically is not related to physical activity, e.g., automobile travel, since most physical activities generate significant motions in more than one or two axes.

The circuitry 60 utilizes the pacing lead 18 which picks up signals from the heart and supplies them through a cardiac signal amplifier 138 that then supplies that signal to an inhibit input 140 of the stimulus pulse generator 130. That signal is also supplied to a reset input 142 of the rate timing circuit 132.

When no pulse from the heart is sensed over a particular time period, the rate timing circuit 132 sends a trigger pulse to a trigger input 143 of the stimulus pulse generator 130 to generate a stimulus or pacing pulse. The heart pulse is also supplied to a NOR gate 144 of a bistable oscillator 146 via a line 148. The stimulus or pacing pulse from the pulse generator 130 is also supplied to the NOR gate 144 via line 150 and an inverted output signal from an output 151 of the oscillator 146 is coupled through a capacitor C2 to a line 152 connected to NOR gate 144.

The output from the capacitor C1 is supplied to a gate G which has its drain D connected to an output 160 of the NOR gate 144 and its source S connected through a resistor R3 to a junction 161 connected to the line 152.

The NOR gate output 160 is connected to an inverter or inverting amplifier 166. The output 151 of the inverting amplifier 166 is connected via a line 168 to a reset and trigger input 169 of the rate timing circuit 132 and is connected to a second side of the capacitor C2 (the first side thereof being connected to the output 151), that is connected to the junction 161 connected to line 152. The output 160 from the NOR gate 144 is also connected through a resistor R4 and a diode D2 to the line 152. The resistor R4 and diode D2 are also connected in parallel across the series connected source S - drain D of the MOSFET Q1 and resistor R3.

The operation of the circuitry to convert the electrical signals generated by one of the piezoelectric sensors 34, 42, 52 or 86, 96, 104 described above into the appropriate pacing rate corresponding to the level of physical activity is described below.

A timing diagram is shown in FIG. 8. This timing diagram shows typical waveforms that can be observed at numbered areas (1), (2), (3), (4) and (5) in the circuitry 60 shown in FIG. 7.

Each signal, graph (1) of FIG. 8, generated by one of the piezoelements 34, 42, 52, 86, 96 or 104 exceeding the trigger level of the programmable monostable multivibrator 114 will trigger an output pulse of preset duration and voltage, graph (2) of FIG. 8. The output pulse results in a forward breakdown of the diode D1 causing it to conduct. The current resulting from the pulse is limited by the resistor R1 and injected into the capacitor C1. After the pulse ends, the diode D1 becomes reverse biased effectively blocking current flow and forcing the charge accumulated on the capacitor C1 to discharge only through resistor R2 in between pulses. Because the resistor R2 has a much higher resistance value than the resistor R1, the voltage level at capacitor C1, graph (3) of FIG. 8, increases rapidly with each pulse but decays relatively slowly in between pulses. Thus, this voltage level represents the average activity level of the pacemaker wearer.

This voltage level, graph (3) of FIG. 8, is applied to the MOSFET Q1 in order to regulate its drain D to source S resistance. The drain and source electrodes D and S of the transistor Q1 are strategically connected to the bistable oscillator 146 which is a circuit well known in the art. The bistable oscillator 146 comprises the NOR gate 144, the inverting amplifier 166, the capacitor C2, the diode D2, the resistor R3 and the resistor R4.

The parallel combination of the resistors R3 and R4 determines a first timing period, T1, duration, graph (4) of FIG. 8. However, the series resistance of the resistor R3 plus the channel resistance of the MOSFET Q1 determines the time period of the pulse T2, graph (4) of FIG. 8. Since the channel resistance of the transistor Q1 is regulated by the voltage level at the capacitor C1 and since that voltage level is a function of the physical activity level of the pacemaker wearer, the transistor Q1 regulates the duration of the time period T2 in proportion to the physical activity. As the level of activity increases, the duration of the pulse T2 shortens which results in a faster frequency at the output 151 of the bistable oscillator 146. The resulting pulses, graph (4) of FIG. 8, are fed via line 168 to the reset and trigger input 155 of the rate timing circuit 132.

When the frequency of the bistable oscillator 146 exceeds that represented by the resting rate value programmed into the rate timing circuit, the timing pulses, graph (4) of FIG. 8, begin to reset each cycle of the rate timing circuit 132, triggering a pacemaker stimulus pulse. In this manner, the stimulus pulse generator 130 outputs stimulus pulses, graph (5) of FIG. 8, at a rate governed by the bistable oscillator 146 (instead of the rate timing circuit 132) when the level of physical activity demands a higher pacing rate.

The programmable monostable multivibrator 114 can be programmed to trigger its output pulses from either the X, Y or Z axis ("OR" mode) or can instead be programmed to require motion signals from at least two axes in order to trigger its output pulse ("AND" mode). In either the "OR" mode or the "AND" mode, the axis or combination of axis along which motion is sensed can also be programmed by the physician. The "OR" mode may be useful in patients who engage in strenuous physical activities that produce small accelerations, such as weight lifting. The "AND" mode can be used to reject nonactivity motion artifacts, such as automobile travel.

The programming lines from the program memory 124 are in the bus 134 and, as shown in FIG. 7, bus lines 170 go to the multiplexer 116, line 171 goes to a trigger level input 172 of the one shot 114, line 173 goes to an AND (Mode)/OR (Mode) input 174 of the one shot 114, line 175 goes to a charge level input 176 of the one shot 114, line 177 goes to a voltage input 178 of the pulse generator 130, line 179 goes to a width input 180 of the pulse generator 130, line 181 goes to a reset input 182 of the rate timing circuit 132, and line 183 goes to a maximum pacing rate input 184 of the rate timing circuit 132.

The monostable multivibrator 114 has the inputs lines 121, 122 and 123 from the first, second and third activity sensors 20 or 70 coupled thereto and has control input lines from the program memory 124 that pass through the multiplexer 16 to the multiplex switches 110, 111 and 112 in the input lines 121, 122 and 123 for setting the trigger level at the inputs from the activity sensors 20 or 70 and has the input lines 170, 172 and 175 from the program memory 124 coupled thereto for setting the monostable multivibrator 114 in and AND mode or in an OR mode and for controlling the charge output or pulse energy content of output pulses from the output of the monostable multivibrator 114.

Noninvasive means for programming the rate of increase in pacing rate input 184 of the rate timing circuit 132. the program memory 124 and supplied via line 175 to input 176. This value alters the charge injected into the capacitor C1, i.e., the pulse shown is graph (3) of FIG. 8, with each output pulse generated by the monostable multivibrator 114. A larger charge dose results in a faster response, and a smaller charge dose results in a slower response. This allows the physician to adapt the pacemaker's rate response to the patient's tolerance.

Noninvasive means for programming resting and maximum pacing rate values is provided by the programming pick up coil 126. The rate timing circuit 132 will sustain the maximum rate value when the rate of the bistable oscillator 146 exceeds the maximum rate value. When the appropriate reduction in the patient's physical activity is detected, the rate of the bistable oscillator 146 will drop below the maximum rate value, causing the rate timing circuit 132 to resume tracking the rate of the bistable oscillator 146 until the rate drops below the resting rate value programmed into the pacer 10 modes.

Circuitry, including the connection to the inhibit input 140 of the stimulus pulse generator 130 are provided to inhibit the stimulus pulse of a natural heartbeat as detected by the cardiac signal amplifier 138 while the pacing rate is between the maximum and resting rate values. This enables the physician to adapt the span of the pacing rate to the patient's tolerance.

In the oscillator 146, the diode D2 operates as a steering diode. When the output 160 of the NOR gate 144 is low or negative, the output 151 of the inverting amplifier 166 and of the oscillator 146 will be positive or high. Just after the output 160 goes low, the output 151 goes positive or high, the potential on line 152 on the second side of capacitor C2, will immediately go positive or high because the high at output 151 will immediately be reflected across the capacitor C2.

Now when the output 160 of the NOR gate 144 goes positive or high, it causes the second side of the capacitor C2 to follow and also go high.

The drain D of the MOSFET Q1 is connected to the output 160 and beginning with the output 160 negative, when the output 160 goes high, a current flows through the MOSFET Q1, out of the source S, through the resistor R3 to C2 to create a low on the line 168 connected to the second side of the capacitor C2, and that low is transmitted to the reset and trigger input 169.

When the output 151 of the inverting amplifier 166 goes from negative to positive, the second side of the capacitor C2 connected to the anode of the diode D2, will also go high because this is an instantaneous change and a fast change, and to a capacitor a fast change means that it acts as a very low impedance such that the potential at the junction 161 between capacitor C2 and diode D2 will follow. Now the anode of diode D2 is positive, but the cathode of diode D2 now is negative, because the output 160 has just gone negative. Now, that allows resistor R4 to control the RC timing constant of the oscillator 146 during that half of the timing cycle, the refractory period, until the voltage at the junction of capacitor C2 and diode D2, which is connected via line 152 to an output of the NOR gate 144, reaches the threshold of the NOR gate 144. Capacitor C2 begins to discharge through diode D2 and resistor R4, and then when that voltage, on the discharge curve, reaches the threshold of the NOR gate 144, then the input to the NOR gate 144 "flips over" and goes low. When the input of the NOR gate 144 goes low, the output 160 of the NOR gate 144 goes high, which makes the output 151 of the inverting amplifier go low. That reverse biases the diode D2 and forward biases the MOSFET Q1, so that the drain D of transistor Q1 now is high and the source of transistor Q1 is now low through resistor R3. Now during this half-cycle, transistor Q1 controls the frequency of the oscillator 146.

The more voltage you have on the gate G of transistor Q1, the faster will be the frequency and the faster will be that half-cycle. The lower the voltage, the longer the cycle.

The potential on output 151 of the inverting amplifier 166 is supplied via line 168 to the reset and trigger input 169. It is supplied faster when we have more voltage on capacitor C1 and slower when we have less voltage on capacitor C1.

The first half of an oscillator cycle 185, the refractory time 186 shown in FIG. 9, is when output 151 is high. With this condition a heart pulse on line 148 or a pacing pulse on line 150 to the NOR gate 144, the output of the oscillator 146 is not affected.

Each cycle 185 of the bistable oscillator 146 has two halves, one-half of that cycle 185 is what is called the refractory time 186 (the first half). During the refractory time 186, we don't want to acknowledge sensing of any cardiac signal. During the second half, which is known as the alert period 188, or the escape period, we do want to sense cardiac signals and if a cardiac event occurs, we want to reset, i.e., end the present cycle and start a new one. Thus, when the output 151 is high, it doesn't matter what pulses come in on lines 148 or 150 to the NOR gate 144. Now, when output 151 goes low, the input to the NOR gate 144 on line 152 will follow and be low too. During that time, if either of the other two input lines 148 or 150 to the NOR gate 144 switches high, that makes the output 160 switch low again and then it starts a new cycle.

From the foregoing description it will be apparent that the activity sensing pacemaker of the present invention has a number of advantages, some of which have been described above and others of which are inherent in the invention. Also modifications can be made to the activity sensing pacemaker of the present invention without departing from the teachings of the invention. Accordingly, the scope of the invention is only to be limited as necessitated by the accompanying claims.

We claim:
1. An activity sensing pacemaker comprising:
  heart pulse sensing means for sensing heart pulses;
  pulse generating means for generating pacing pulses;
  activity sensing means for sensing body movements of a patient wearing said pacemaker relative to the chest of the patient in specific ones of three dimensions/directions extending along an x axis, a y axis, or a z axis, and independent of the force of gravity, said activity sensing means including first means for sensing activity along a first one of said three axes and second means for sensing activity along a second one of said three axes; and,
  control means coupled to said heart pulse sensing means, to said pulse generating means and to said activity sensing means for controlling the pacing frequency of the pacing pulses generated by said pulse generating means either in response to the intrinsic heart rhythm of the patient sensed by said heart pulse sensing means or in response to the direction and frequency of the patient's body motions sensed by said activity sensing means in or along at least two of said three axes, x, y, or z, relative to the patient's chest.

2. The pacemaker of claim 1 wherein said activity sensing means includes a third means for sensing activity along said third axis.

3. The pacemaker of claim 1 wherein said first means and said second means for sensing activity along one of said respective axes are each defined by a piezoelectric element mounted transverse to the respective axis along which activity is to be sensed for, generating electrical signals when there is movement of the pacemaker along the axis causing movement of the piezoelectric element.

4. The pacemaker of claim 1 wherein said activity sensing means includes at least one plate and said first means and said second means comprises piezoelectric elements which are each mounted transverse to two separate axes of the plate transverse to each other.

5. The pacemaker of claim 4 wherein said plate has a hole therein and said first piezoelectric element forming said first means has a portion thereof mounted over said hole so that it can flex in an axis that intersects said hole and is transverse to the plane of the plate.

6. The pacemaker of claim 5 wherein said second piezoelectric element extends outwardly from said plate where it is free to move in an axis generally parallel to the plane of the plate.

7. The pacemaker of claim 5 wherein said activity sensing means includes a third means for sensing activity along said third axis and said third means comprises a piezoelectric element extending transversely of the plate and positioned to move along an axis transverse to said second axis and also transverse to said first axis.

8. The pacemaker of claim 7 wherein said plate is generally rectangular and has notches in two side edges thereof and said second and third piezoelectric elements have a base tab which is mounted adjacent one of said notches with an elongate leg portion containing the piezoelectric element extending outwardly within said notch from the plane of said plate.

9. The pacemaker of claim 7 wherein said plate has an x axis, a y axis and a z axis extending transversely of said plate and said first piezoelectric element is positioned to move in said hole in said plate along said Z axis of said plate, said second piezoelectric element is positioned to move along an axis in a plane parallel to said X axis of said plate and said third piezoelectric element is positioned for movement along an axis in a plane parallel to said Y axis of said plate.

10. The pacemaker of claim 7 wherein said plate is nonmetallic and has conductive strips printed thereon which are connected to said first, second and third piezoelectric elements.

11. The pacemaker of claim 1 wherein said activity sensing means includes two spaced apart plates which are connected together and parallel spaced apart by several connector spacing elements, said first plate has a hole therein and said first means for sensing activity along a first axis comprises a piezoelectric film extending across said hole in said first plate and having a weight in the middle thereof for movement toward and away from said hole in said first plate.

12. The pacemaker of claim 11 wherein said second means for sensing activity along a second axis comprises a piezoelectric film that is mounted between said two plates and has a weight intermediate the ends thereof which is positioned for movement along an axis in a plane extending between said two plates.

13. The pacemaker of claim 12 including a third means for sensing activity along a third axis, said third means comprising a piezoelectric element which extends between said first and second plates and includes a piezoelectric film extending between said two plates and having a weight intermediate the ends thereof which is movable along an axis in the plane between the two plates with said third axis being transverse to said second axis and to said first axis.

14. The pacemaker of claim 14 wherein said first axis is a Z axis of each plate, said second axis extends parallel to the X axis of each plate, and the third axis extends parallel to the Y axis of each plate.

15. The pacemaker of claim 1 wherein said activity sensing means further includes third means for sensing activity along a third axis which is transverse to the first axis and to the second axis, and wherein said control means includes multiplexing means for selecting or multiplexing the signals from each of said first, second and third means respectively whereby said pulse generating means is controlled relative to the activity/movement in one, two or three axes or all the axes along which means for sensing activity/movement are provided in said pacemaker.

16. The pacemaker of claim 15 wherein said control means comprises at least three input lines, an electronic switch in each input line, and a program memory which has outputs coupled to said multiplexing means and to said switches in each one of said input lines from said first, second and third sensing means.

17. The pacemaker of claim 16 wherein said first, second and third means are defined by piezoelectric elements each having an output connected to one of said input lines.

18. The pacemaker of claim 16 wherein said control means further includes data pick up means coupled to said program memory for noninvasively picking up data instructions from a data sending means located outside of the body of the wearer of said pacemaker.

19. The pacemaker of claim 18 wherein said data pick up means includes a programming pick up coil.

20. The pacemaker of claim 19 wherein said data pick up means further includes a receiver amplifier/demodulator coupled between said programming pick up coil and said program memory.

21. The pacemaker of claim 16 wherein said control means includes an operating program in said program memory and a programmable monostable multivibrator which has an output for output pulses, which operates in an AND mode or in an OR mode, which has inputs coupled to the input lines from said first, second and third sensing means and which has control input lines from said program memory for charge level, for voltage level and for pulse width coupled thereto for setting the trigger level at the inputs from said sensing means elements, for setting the monostable multivibrator in an AND mode or in an OR mode, and for controlling the charge output or pulse energy content of output pulses from an output of said monostable multivibrator.

22. The pacemaker of claim 21 wherein said control means includes means in said program memory and said multivibrator for enabling said multivibrator to pass only signals received relative to activity/movement along one axis or two axes or all axes and/or for requiring that there be signals on all three axes in order for there to be output pulses at said output of said monostable multivibrator.

23. The pacemaker of claim 21 wherein said control means further comprises a stimulus pulse generator having an output terminal and an inhibit terminal both adapted to be coupled to a cardiac pacing lead and having inputs coupled to said program memory, a rate timing circuit having inputs coupled to said program memory and an output coupled to said stimulus pulse generator, an integrating circuit coupled to said output of said monostable multivibrator, and a bistable oscillator having a control input coupled to said integrating circuit and an output coupled to a reset and trigger terminal of said rate timing circuit.

24. The pacemaker of claim 23 including a current throttling electronic switch and wherein said control input is a gate of said current throttling electronic switch in said bistable oscillator that is coupled to said integrating circuit and said integrating circuit includes an RC charging circuit including a capacitor and an RC discharge circuit including the same capacitor and the positive side of said capacitor being coupled to said gate of said electronic current throttling switch in said bistable multivibrator.

25. The pacemaker of claim 24 wherein said integrating circuit includes a resistor, a diode and said capacitor connected in series and coupled between said output of said monostable multivibrator and a system ground or common, and said RC circuit includes a second resistor connected in parallel across said capacitor.

26. The pacemaker of claim 24 wherein said heart pulse sensing means senses heart pulses by means of a conductor in a pacing lead and said bistable oscillator includes a NOR gate having an output and three inputs one being a feedback input from said bistable oscillator, another being a reset input from said conductor in said pacing lead which senses heart pulses and a second reset input which is connected to said output from said stimulus pulse generator, said current throttling electronic switch being a field effect transistor having said gate thereof coupled to said capacitor in said integrating circuit, a drain coupled to said output of said NOR gate and a source coupled through a resistor to said feedback line to said NOR gate, an inverter having an input coupled to said output of said NOR gate and an output that defines the output of said bistable oscillator which is coupled to said reset and trigger input terminal of said rate timing circuit, a capacitor which is coupled between said inverter/oscillator output and said feedback line to said NOR gate, a resistor and diode coupled in series across said inverter and capacitor, said diode being coupled to said feedback line to one of said inputs to said NOR gate.

27. An activity sensing pacemaker comprising:
heart pulse sensing means for sensing heart pulses;
pulse generating means for generating pacing pulses;
activity sensing means for sensing activity/movement of a patient wearing said pacemaker in one or more of three directions/dimensions, x, y, z, and for causing said pulse generating means to generate pacing pulses at a rate/frequency related to the movements sensed; and,
control means coupled to said heart pulse sensing means, to said pulse generating means and to said activity sensing means for controlling said pulse generating means in response to the heart pulses sensed or in response to the patient movements sensed, said activity sensing means causing generation of control pulses related to the movements of the patient and said control means including frequency sensing means for sensing the frequency of the control pulses generated and for controlling the rate/frequency of the pacing pulses generated by said pulse generating means relative to the frequency of said control pulses generated by the movements of the patient in one or more directions/dimensions, x, y, z, independent of the duration or amplitude of said control pulses.

28. The pacemaker of claim 27 wherein said frequency sensing means include a monostable multivibrator coupled to said activity sensing means and an integrating circuit coupled to said multivibrator.

29. The pacemaker of claim 28 wherein said pulse generating means comprises a stimulus pulse generator and said control means further include a rate timing circuit having a trigger and reset input and being coupled to said stimulus pulses generator, and a bistable oscillator having a control input coupled to an output of said integrating circuit and an output coupled to said trigger and reset input of said rate timing circuit.

30. The pacemaker of claim 29 wherein said bistable oscillator includes a NOR gate having three inputs including a first input coupled to said stimulus pulse generator for receiving pacing pulses from said stimulus pulse generator, a second input coupled to said heart pulse sensing means for receiving heart pulses from the heart of the patient, and a third feedback input coupled to said bistable oscillator for receiving an output from said bistable oscillator.

* * * * *

UNITED STATES PATENT AND TRADEMARK OFFICE
CERTIFICATE OF CORRECTION

PATENT NO. : 5,318,596
DATED : June 7, 1994
INVENTOR(S) : Francisco J. Barreras and Oscar Jimenez It is certified that error appears in the above-indentified patent and that said Letters Patent is hereby corrected as shown below:

Column 10, lines 6-7 "rate input 184 of the rate timing circuit 132" should be —frequency is provided via a charge value contained in—.

Signed and Sealed this

Thirtieth Day of August, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,318,596

DATED : June 7, 1994

INVENTOR(S) : Francisco J. Barreras and Oscar Jimenez

It is certified that error appears in the above-indentified patent and that said Letters Patent is hereby corrected as shown below:

On the Title Page, "(73) Assignee: Exonic Corporation, Miami, Fla." should be --(73) Assignee: Exonix Corporation, Miami, Fla.--.

Signed and Sealed this

Twenty-second Day of August, 1995

Attest:

BRUCE LEHMAN

*Attesting Officer*    *Commissioner of Patents and Trademarks*